US010793895B2

(12) United States Patent
Locke et al.

(10) Patent No.: US 10,793,895 B2
(45) Date of Patent: Oct. 6, 2020

(54) SYSTEMS AND METHODS FOR EPIGENETIC ANALYSIS

(71) Applicant: Seven Bridges Genomics Inc., Charlestown, MA (US)

(72) Inventors: Devin Locke, Medford, MA (US); Wan-Ping Lee, Somerville, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 540 days.

(21) Appl. No.: 15/007,874

(22) Filed: Jan. 27, 2016

(65) Prior Publication Data

US 2017/0058320 A1   Mar. 2, 2017

Related U.S. Application Data

(60) Provisional application No. 62/209,058, filed on Aug. 24, 2015.

(51) Int. Cl.
| | | |
|---|---|---|
| *G01N 33/48* | (2006.01) | |
| *G01N 31/00* | (2006.01) | |
| *C12Q 1/6806* | (2018.01) | |
| *C12Q 1/6874* | (2018.01) | |
| *G16B 30/00* | (2019.01) | |
| *C12Q 1/6869* | (2018.01) | |

(52) U.S. Cl.
CPC ......... *C12Q 1/6806* (2013.01); *C12Q 1/6869* (2013.01); *C12Q 1/6874* (2013.01); *G16B 30/00* (2019.02)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,511,158 A | 4/1996 | Sims |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,582,938 B1 | 6/2003 | Su et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,321,623 B2 | 1/2008 | Dambrackas |
| 7,483,585 B2 | 1/2009 | Brakus, Jr. |
| 7,577,554 B2 | 8/2009 | Lystad et al. |
| 7,580,918 B2 | 8/2009 | Chang et al. |
| 7,598,035 B2 | 10/2009 | Macevicz |
| 7,620,800 B2 | 11/2009 | Huppenthal et al. |
| 7,776,616 B2 | 8/2010 | Heath et al. |
| 7,809,509 B2 | 10/2010 | Milosavljevic |
| 7,835,871 B2 | 11/2010 | Kain et al. |
| 7,885,840 B2 | 2/2011 | Sadiq et al. |
| 7,917,302 B2 | 3/2011 | Rognes |
| 7,957,913 B2 | 6/2011 | Chinitz et al. |
| 7,960,120 B2 | 6/2011 | Rigatti et al. |
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 8,972,201 B2 | 3/2015 | Mande et al. |

(Continued)

FOREIGN PATENT DOCUMENTS

| | | |
|---|---|---|
| KR | 101282798 B1 | 7/2013 |
| WO | 2007/086935 A2 | 8/2007 |

(Continued)

OTHER PUBLICATIONS

Truszkowski, 2011, New developments on the cheminformatics open workflow environment CDK-Taverna, J Cheminform 3:54.
Turi, 2007, Tavema Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.

(Continued)

*Primary Examiner* — Anna Skibinsky
(74) *Attorney, Agent, or Firm* — Wolf, Greenfield & Sacks, P.C.

(57) ABSTRACT

The invention provides systems and methods for determining patterns of modification to a genome of a subject by representing the genome using a graph, such as a directed acyclic graph (DAG) with divergent paths for regions that are potentially subject to modification, profiling segments of the genome for evidence of epigenetic modification, and aligning the profiled segments to the DAG to determine locations and patterns of the epigenetic modification within the genome.

18 Claims, 9 Drawing Sheets

(56) References Cited

U.S. PATENT DOCUMENTS

| | | | |
|---|---|---|---|
| 9,063,914 B2 | 6/2015 | Kural et al. | |
| 9,092,402 B2 | 7/2015 | Kural et al. | |
| 9,116,866 B2 | 8/2015 | Kural | |
| 9,390,226 B2 | 7/2016 | Kural | |
| 9,817,944 B2 | 11/2017 | Kural | |
| 2002/0164629 A1 | 11/2002 | Quake et al. | |
| 2002/0190663 A1 | 12/2002 | Rasmussen | |
| 2003/0032026 A1* | 2/2003 | Berlin | C12Q 1/6827 435/6.11 |
| 2004/0023209 A1 | 2/2004 | Jonasson | |
| 2005/0089906 A1 | 4/2005 | Furuta et al. | |
| 2006/0024681 A1 | 2/2006 | Smith et al. | |
| 2006/0195269 A1 | 8/2006 | Yeatman et al. | |
| 2006/0292611 A1 | 12/2006 | Berka et al. | |
| 2007/0087365 A1* | 4/2007 | Van Criekinge | C12Q 1/6886 435/6.12 |
| 2007/0114362 A1 | 5/2007 | Feng et al. | |
| 2007/0166707 A1 | 7/2007 | Schadt et al. | |
| 2008/0003571 A1 | 1/2008 | McKeman et al. | |
| 2008/0077607 A1 | 3/2008 | Gatawood et al. | |
| 2008/0251711 A1 | 10/2008 | Reilly | |
| 2008/0281463 A1 | 11/2008 | Suh et al. | |
| 2008/0294403 A1 | 11/2008 | Zhu et al. | |
| 2009/0026082 A1 | 1/2009 | Rothberg et al. | |
| 2009/0119313 A1 | 5/2009 | Pearce | |
| 2009/0127589 A1 | 5/2009 | Rothberg et al. | |
| 2009/0164135 A1 | 6/2009 | Brodzik et al. | |
| 2009/0191565 A1 | 7/2009 | Lapidus et al. | |
| 2009/0233809 A1 | 9/2009 | Faham et al. | |
| 2009/0300781 A1 | 12/2009 | Bancroft et al. | |
| 2009/0318310 A1 | 12/2009 | Liu et al. | |
| 2009/0325145 A1 | 12/2009 | Sablon et al. | |
| 2010/0010992 A1 | 1/2010 | Morris | |
| 2010/0035252 A1 | 2/2010 | Rothberg et al. | |
| 2010/0041048 A1 | 2/2010 | Diehl et al. | |
| 2010/0137143 A1 | 6/2010 | Rothberg et al. | |
| 2010/0169026 A1 | 7/2010 | Sorenson et al. | |
| 2010/0188073 A1 | 7/2010 | Rothberg et al. | |
| 2010/0197507 A1 | 8/2010 | Rothberg et al. | |
| 2010/0240046 A1 | 9/2010 | Palmer et al. | |
| 2010/0282617 A1 | 11/2010 | Rothberg et al. | |
| 2010/0285578 A1 | 11/2010 | Selden et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0004413 A1 | 1/2011 | Carnevali et al. | |
| 2011/0009278 A1 | 1/2011 | Kain et al. | |
| 2011/0098193 A1 | 4/2011 | Kingsmore et al. | |
| 2011/0207135 A1 | 8/2011 | Faham et al. | |
| 2011/0257889 A1 | 10/2011 | Klammer et al. | |
| 2012/0030566 A1 | 2/2012 | Victor | |
| 2012/0040851 A1 | 2/2012 | Lieberman et al. | |
| 2012/0041727 A1 | 2/2012 | Mishra et al. | |
| 2012/0045771 A1 | 2/2012 | Beier et al. | |
| 2012/0157322 A1 | 6/2012 | Myllykangas et al. | |
| 2012/0239706 A1 | 9/2012 | Steinfadt | |
| 2012/0330566 A1 | 12/2012 | Chaisson | |
| 2013/0029879 A1 | 1/2013 | Shetty et al. | |
| 2013/0035904 A1 | 2/2013 | Kuhn | |
| 2013/0059738 A1 | 3/2013 | Leamon et al. | |
| 2013/0059740 A1 | 3/2013 | Drmanac et al. | |
| 2013/0073214 A1 | 3/2013 | Hyland et al. | |
| 2013/0124100 A1 | 5/2013 | Drmanac et al. | |
| 2013/0232480 A1 | 9/2013 | Winterfeldt et al. | |
| 2013/0289099 A1 | 10/2013 | Goff et al. | |
| 2013/0311106 A1 | 11/2013 | White et al. | |
| 2013/0332081 A1 | 12/2013 | Reese et al. | |
| 2013/0345066 A1 | 12/2013 | Brinza et al. | |
| 2014/0012866 A1 | 1/2014 | Bowman et al. | |
| 2014/0025312 A1 | 1/2014 | Chin et al. | |
| 2014/0051588 A9 | 2/2014 | Drmanac et al. | |
| 2014/0066317 A1 | 3/2014 | Talasaz | |
| 2014/0129201 A1 | 5/2014 | Kennedy et al. | |
| 2014/0136120 A1 | 5/2014 | Colwell et al. | |
| 2014/0200147 A1 | 7/2014 | Bartha et al. | |
| 2014/0278590 A1 | 9/2014 | Abbassi et al. | |
| 2014/0280360 A1 | 9/2014 | Webber et al. | |
| 2014/0281708 A1 | 9/2014 | Adam et al. | |
| 2014/0323320 A1 | 10/2014 | Jia et al. | |
| 2014/0371110 A1 | 12/2014 | Van Rooyen et al. | |
| 2015/0020061 A1 | 1/2015 | Ravi | |
| 2015/0056613 A1 | 2/2015 | Kural | |
| 2015/0057946 A1 | 2/2015 | Kural | |
| 2015/0066383 A1 | 3/2015 | Wernicke | |
| 2015/0094212 A1 | 4/2015 | Gottimukkala et al. | |
| 2015/0110754 A1 | 4/2015 | Bai et al. | |
| 2015/0112602 A1 | 4/2015 | Kural et al. | |
| 2015/0112658 A1 | 4/2015 | Kural et al. | |
| 2015/0197815 A1 | 7/2015 | Kural | |
| 2015/0199472 A1 | 7/2015 | Kural | |
| 2015/0199473 A1 | 7/2015 | Kural | |
| 2015/0199474 A1 | 7/2015 | Kural | |
| 2015/0199475 A1 | 7/2015 | Kural | |
| 2015/0227685 A1 | 8/2015 | Kural | |
| 2015/0293994 A1 | 10/2015 | Kelly | |
| 2015/0302145 A1 | 10/2015 | Kural et al. | |
| 2015/0310167 A1 | 10/2015 | Kural et al. | |
| 2015/0344970 A1 | 12/2015 | Vogelstein et al. | |
| 2015/0347678 A1 | 12/2015 | Kural | |
| 2015/0356147 A1 | 12/2015 | Mishra et al. | |
| 2016/0259880 A1 | 9/2016 | Semenyuk | |
| 2016/0306921 A1 | 10/2016 | Kural | |
| 2016/0342737 A1 | 11/2016 | Kaye | |
| 2016/0355881 A1* | 12/2016 | Wangh | C12Q 1/6827 |
| 2016/0364523 A1 | 12/2016 | Locke et al. | |
| 2017/0058320 A1 | 3/2017 | Locke et al. | |
| 2017/0058341 A1 | 3/2017 | Locke et al. | |
| 2017/0058365 A1 | 3/2017 | Locke et al. | |
| 2017/0198351 A1 | 7/2017 | Lee et al. | |
| 2017/0199959 A1 | 7/2017 | Locke | |
| 2017/0199960 A1 | 7/2017 | Ghose et al. | |
| 2017/0242958 A1 | 8/2017 | Brown | |

FOREIGN PATENT DOCUMENTS

| | | |
|---|---|---|
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |
| WO | 2015/027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Wu, 2010, Fast and SNP-tolerant detection of complex variants and splicing in short reads, Bioinformatics, 26(7):873-881.

(56) References Cited

OTHER PUBLICATIONS

Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zhang, 2013, Taverna Mobile: Taverna workflows on Android, EMBnet J 19(B):43-45.
Zhao, 2012, Why Workflows Break—Understanding and Combating Decay in Taverna Workflows, eScience 2012, Chicago, Oct. 2012.
Abouelhoda, 2012, Tavaxy: integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13): i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29 (10):1250-1259.
BCF2 Quick Reference (r198), available at http://samtools.github.io/hts-specs/BCFv2_qref.pdf.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1: e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12): e1000589.
Durbin, 2014, Efficient haplotype matching and storage using the positional Burrows-Wheeler transform (PBWT), Bioinformatics 30(9):1266-1272.
Durham, 2005, EGene: a configurable pipeline system for automated sequence analysis, Bioinformatics 21(12):2812-2813.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Lee, 2005, Bioinformatics analysis of alternative splicing, Brief Bioinf 6(1):23-33.

(56) References Cited

OTHER PUBLICATIONS

Lee, 2014, Mosaik: A hash-based algorithm for accurate next-generation sequencing short-read mapping, PLoS One 9(3):e90581.
LeGault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11(5):473-483.
Li, 2015, BGT: efficient and flexible genotype query across many samples, arXiv:1506.08452 [q-bio.GN].
Li, 2015, Towards Better Understanding of Artificats in Variant Calling from High-Coverage Samples, arXiv:1404.0929 [q-bio.GN].
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.

(56) References Cited

OTHER PUBLICATIONS

Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search filed Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
International Search Report and Written Opinion of the International Searching Authority dated Nov. 17, 2015 or International Application No. PCT/US2015/048891 (11 Pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24(8):1118-20.
Larkin, 2007, Clustal W and Clustal X version 2.0, Bioinformatics 23(21):2947-2948.
Layer, 2015, Efficient compression and analysis of large genetic variation datasets, Biorxiv preprint, available at http://biorxiv.org/content/early/2015/04/20/018259.
Layer, 2015, Efficient genotype compression and analysis of large genetic-variation data sets, Nat Meth 13(1):63-65.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Peixoto, 2014, Efficient Monte Carlo and greedy heuristic for the inference of stochastic block models, Phys. Rev. E 89, 012804.
Pope, 2014, Rover Variant Caller: Read-Pair Overlap Considerate Variant-Calling Software Applied to PCR-Based Massively Parallel Sequencing Datasets, Source Code Bio Med 9:3.
Popitsch, 2013, NGC: lossless and lossy compression of aligned high-throughput sequencing data, Nucl Acids Res, 41(1):e27.
Posada, 1998, Model Test: testing the model of DNA substitution, Bioinformatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.

(56) References Cited

OTHER PUBLICATIONS

Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5)596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing.pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
Tewhey, 2011, The importance of phase information for human genomics, Nat Rev Gen 12:215-223.
The 1000 Genomes Project, 2015, A global reference for human genetic variation, Nature 526:68-74.
The Variant Call Format (VCF) Version 4.2 Specification (Jan. 26, 2015), available at https://samtools.github.io/hts-specs/VCFv4.2.pdf.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
Duan et al., Optimizing de novo common wheat transcriptome assembly using short-read RNA-Seq data. (2012) pp. 1-12, vol. 13, BMC Genomics.
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Grasso, 2004, Combining partial order alignment and progressive multiple sequence alignment increases alignment speed and scalability to very large alignment problems, Bioinformatics 20(10):1546-1556.
International Search Report and Written Opinion dated Aug. 31, 2017 for International Application No. PCT/US2017/018830 with International Filing Date Feb. 22, 2017, (11 pages).
International Search Report and Written Opinion dated Apr. 19, 2017 for International Patent Application No. PCT/US2017/012015, (14 Pages).
International Search Report and Written Opinion dated Jan. 10, 2017, for International Patent Application No. PCT/US16/57324 with International Filing Date Oct. 17, 2016, (7 pages).
International Search Report and Written Opinion dated Apr. 7, 2017, for International Patent Application No. PCT/US17/13329, filed Jan. 13, 2017, (9 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, PCT/US2014/060690 (11 pages).
Koolen, 2008, Clinical and Molecular Delineation of the 17q21.31 Microdeletion Syndrome, J Med Gen 45(11):710-720.

(56) References Cited

OTHER PUBLICATIONS

Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2014, Accurate read mapping using a graph-based human pan-genome, ASHG 2014 Abstracts.
Lupski, 2005, Genomic disorders: Molecular mechanisms for rearrangements and conveyed phenotypes, PLoS Genetics 1(6):e49.
Marth et al., 1999—A general approach to single-nucleotide polymorphism discovery, pp. 452-456, vol. 23, Nature Genetics.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Parks, 2015, Detecting non-allelic homologous recombination from high-throughput sequencing data, Genome Biol 16:17.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.
U.S. Appl. No. 15/014,500, filed Feb. 3, 2016, Locke et al.
Floyd, Algorithm 245: treesort. Communications of the ACM. Dec. 1964 1;7(12):701.
Huddleston et al., A new data structure for representing sorted lists. Acta informatica. Jun. 1982 1;17(2):157-84.
Cormen et al., Introduction to Algorithms. Third Edition. The MIT Press. 2009. 6 pages.
Crochemore et al., Direct Construction of Compact Directed Acyclic Word Graphs. Springer, Berlin, Heidelberg. 1997:116-29.
Croft et al., The Use of Phrases and Structured Queries in Information Retrieval. Proceedings of the 14th Annual International ACM SIGIR Conference on Research and Development in Information Retrieval. 1991:32-45.
Do et al., Compressed Directed Acyclic Word Graph with Application in Local Alignment. Algorithmica. 2013;67:125-41.
Hendren et al., Parallelizing Programs with Recursive Data Structures. IEEE Transactions on Parallel and Distributed Systems. 1990;1(1):35-47.
Jones et al., AliWABA: alignment on the web through an A-Bruijn approach. Nucleic Acids Research. 2006;34:613-6.
Kim et al., Introducing EzTaxon-e: a prokaryotic 16S rRNA gene sequence database with phylotypes that represent uncultured species. International Journal of Systematic and Evolutionary Microbiology. 2012;62:716-21.
Neumann, Efficient Generation and Execution of DAG-Structured Query Graphs. Doctoral Dissertation. Universitat Mannheim. 2005. 170 pages.
Quast et al., The SILVA ribosomal RNA gene database project: improved data processing and web-based tools. Nucleic Acids Research. 2013;41:590-6.
Schmieder et al., Identification and removal of ribosomal RNA sequences from metatranscriptomes. Bioinformatics. 2012;28(3):433-5.
Standish, Data Structures, Algorithms and Software Principles in C. Chapter 10 Section 10.1: Introduction and Motivation and Section 10.2: Basic Concepts and Terminology. Addison-Wesley Publishing Company. 1995:405-411.
Wajid et al., Review of General Algorithmic Features for Genome Assembles for Next Generation Sequencers. Genomics Proteomics and Bioinformatics. Science Direct. Elsevier. 2012;10:58-73.
Wheeler et al., the complete genome of an individual by massively parallel DNA sequencing. Nature. Letters. 2008;452:872-6.

\* cited by examiner

FIG. 7

SYSTEMS AND METHODS FOR EPIGENETIC ANALYSIS

CROSS-REFERENCE TO RELATED APPLICATIONS

This application claims priority to and the benefit of U.S. Provisional Application Ser. No. 62/209,058, filed Aug. 24, 2015, the contents of which are incorporated by reference.

TECHNICAL FIELD

The invention relates to epigenetic analysis.

BACKGROUND

Epigenetic modifications to the human genome are linked to cancer and other clinical pathologies. For example, hypomethylation of the genome is highly prevalent across all cancer types but also exhibits regional specificity depending on tumor type and stage as discussed in Hoffman, 2005, Causes and consequences of DNA hypomethylation in human cancer, Biochem Cell Biol 83(3):296-321. Epigenetic modifications are also thought to irreversibly alter the expression of genes during the normal differentiation of embryonic stem cells into specific tissues. Patterns of epigenetic modifications can potentially reveal such conditions as fetal chromosome disorders. See Hultén et al., 2011, Non-invasive prenatal diagnosis: An epigenetic approach to the detection of common fetal chromosome disorders by analysis of maternal blood samples, in Circulating Nucleic Acids in Plasma and Serum, Proc 6 Int Conf CNIPS, pp. 133-142, Gahan, Ed. Springer.

Unfortunately, existing approaches to studying patterns of epigenetic modification are limited. It is proposed that methylated cytosine in genomic DNA can be detected by bisulfite sequencing. Treatment of DNA with bisulfite converts un-methylated cytosines to uracil without affecting methylated cytosines in the manner shown in FIG. 9. During subsequent amplification and sequencing steps, the uracil residues act as templates for incorporate of adenines, which implies that where sequencing yields a cytosine base call, it can be supposed that the original DNA included a methylated cytosine at that location. However, the sequencing procedures will yield adenine base calls for both the original thymines and the original unmethylated cytosines.

SUMMARY

The invention provides systems and methods for determining patterns of modification to a genome of a subject by representing the genome using a graph, such as a directed acyclic graph (DAG), with divergent paths for regions that are potentially subject to modification, profiling segments of the genome for evidence of epigenetic modification, and aligning the profiled segments to the DAG to determine locations and patterns of the epigenetic modification within the genome. The DAG can be created by sequencing at least a portion of the genome. To determine a pattern of methylation in the genome, segments can be profiled by a bisulfite sequencing, or Methyl-Seq, operation to produce a sequence in which a C represents a methylated cytosine in the original genome. That sequence can be aligned to the DAG to determine the pattern of methylation in the genome. Thus by determining the presence of methylated bases via the bisulfite sequencing operation, and determining the location of those bases in the genome by reference to the DAG, the invention may be used to provide a report that describes a pattern of epigenetic modification within the subject's genome. Since the DAG includes diverging paths for loci that are potentially modified, the sequence that profiles modification within a segment of the genome will align to the DAG. If the potentially modified residue was in-fact modified, then it will align to one of the diverging branches and if that residue was not modified it will align to the other of the diverging branches. Thus, use of a DAG allows for sensitive and accurate determinations of the locations—and therefore patterns—of epigenetic modification. The described method can be used to show a pattern of methylation across a substantial portion of gene, operon, chromosome, or genome. Thus methods of the invention can be used to provide valuable insights into an organism's development or a subject's health and can potentially reveal hypomethylation or other patterns of modification that may give an early warning of cancer or other clinically significant issues.

In certain aspects, the invention provides a method for determining genomic modifications in a subject. The method includes obtaining a sequence of nucleotide bases from nucleic acid from a subject and transforming the sequence into a graph. The graph is composed of vertices connected by edges and includes at least one path that splits into a first branch and a second branch, wherein the first branch represents a base observed in a position of the sequence and the second branch represents an alternative base not observed in the position. The first branch and the second branch may subsequently rejoin, e.g., just 3' to the position. A second sequence is obtained from bisulfite-treated nucleic acid from the subject and the method further includes determining an optimal alignment between the second sequence and the graph and observing—in a position in the second sequence that aligns to the position in the sequence—a corresponding base that matches the base observed in the position. The second sequence of nucleotide bases may be obtained by treating a portion of the nucleic acid from the subject with bisulfite and sequencing the bisulfite-treated nucleic acid from the subject. A report is provided that identifies a modified base at the position within the genome of the subject.

In some embodiments, the treatment selectively converts unmodified versions of the base to another nucleotide base. For example, the second sequence can be obtained from bisulfite-treated DNA from the subject. In certain embodiments, the base represented by the first branch of the graph is cytosine and the alternative base represented by the second branch is thymine, and the report identifies a methylated cytosine at the position within an exon, gene, operon, genome, or other segment of interest from the subject. Methods may include identifying methylated cytosines at a plurality of positions within the genome of the subject. In some embodiments, methods include identifying all other instances of the modified base occurring across at least 50% of a length of a chromosome of the genome of the subject. The report may identify an unmodified version of the base at a different position in the genome of the subject (e.g., the report may show what is and is not modified across a gene, operon, chromosome, or genome). The sequence and the second sequence may be derived from sequence reads generated by operating a nucleic acid sequencing instrument.

Preferably the steps are performed using a computer system comprising a processor coupled to a memory subsystem, and the graph is stored in the memory subsystem using adjacency lists. In some embodiments, there is an adjacency list for each vertex and edge, in which the adjacency list for a vertex or edge lists the edges or vertices to which that vertex or edge is adjacent. Each entry in the adjacency list is a pointer to the adjacent vertex or edge. Preferably, each pointer identifies a physical location in the memory subsystem at which the adjacent object is stored.

Methods of the invention may use an iterative process to accommodate treatment procedures that do not always treat each and every modified base. For example, where some given bisulfite treatment does not always convert every methylated cytosine, the method may include performing a plurality of replicate bisulfite treating, sequencing, and alignment operations and calling a methylated cytosine when a plurality of replicate sequences include a cytosine aligned to the position of the sequence.

Methods may be used to provide a report on phenomenon with clinical or developmental significance to a subject. For example, a report may identify a gene in the subject for which transcription has been regulated by the methylated cytosine at the position within the genome of the subject. In some embodiments, the report identifies a methylation status of a CpG island within the genome of the subject, for example, whether the CpG island is hyper- or hypo-methylated, or a pattern of methylation within the CpG island.

Aspects of the invention provide a computer system for determining genomic modifications in a subject. The computer system includes a processor coupled to a memory subsystem and is operable to obtain a sequence of nucleotide bases from nucleic acid from a subject and transform the sequence into a graph. The graph includes vertices connected by edges and at least one path that splits into a first branch and a second branch, wherein the first branch represents a base observed in a position of the sequence and the second branch represents an alternative base not observed in the position. The first branch and the second branch may subsequently rejoin, e.g., just 3' to the position. The graph is preferably stored in the memory subsystem using adjacency lists. In some embodiments, there is an adjacency list for each vertex and edge, in which the adjacency list for a vertex or edge lists the edges or vertices to which that vertex or edge is adjacent. Each entry in adjacency list is a pointer to the adjacent vertex or edge. Preferably, each pointer identifies a physical location in the memory subsystem at which the adjacent object is stored. The system may be operated to obtain a second sequence from bisulfite-treated nucleic acid from the subject and determine an optimal alignment between the second sequence and the graph. The system is operable to observe—in a position in the second sequence that aligns to the position in the sequence—a corresponding base that matches the base observed in the position. The system provides a report that identifies a modified base at the position within the genome of the subject.

In some embodiments, the treatment selectively converts unmodified versions of the base to another nucleotide base. In certain embodiments, the base represented by the first branch of the graph is cytosine and the alternative base represented by the second branch is thymine, and the report identifies a methylated cytosine at the position within the genome of the subject. In certain embodiments, the system is operable to identify methylated cytosines at a plurality of positions within the genome of the subject. In some embodiments, the system identifies all other instances of the modified base occurring across at least 50% of a length of a chromosome of the genome of the subject. The report may identify an unmodified version of the base at a different position in the genome of the subject (e.g., the report may show what is and is not modified across a gene, operon, chromosome, or genome). The sequence and the second sequence may be derived from sequence reads generated by operating a nucleic acid sequencing instrument.

The system may provide a report on phenomenon with clinical or developmental significance to a subject. For example, a report may identify a gene in the subject for which transcription has been regulated by the methylated cytosine at the position within the genome of the subject. In some embodiments, the report identifies a methylation status of a CpG island within the genome of the subject.

BRIEF DESCRIPTION OF THE DRAWINGS

FIG. 7 shows the matrices used by a modified Smith-Waterman operation for performing an alignment against a graph.

DETAILED DESCRIPTION

The invention provides systems and methods for the graph-based analysis of epigenetic phenomenon. Systems and methods of the invention may be used with Methyl-Seq data to profile patterns of epigenetic modifications in a genome of a subject. The invention includes the insight that the complex and frequently-compromised data produced by Methyl-Seq sequencing is particularly well suited to benefit from the disclosed graph-based alignment methods. In certain embodiments, the invention uses a graph, such as a directed acyclic graph (DAG) to represent a genome or region thereof with potentially modified loci being included in the DAG in branches for each of the modified and unmodified forms. A technique such as Methyl-Seq can be used to profile a segment of the genome to identify modified residues, and the profiled segment can be compared to the DAG, using for example a modified Smith-Waterman operation to determine locations and patterns of the modified residues within the genome.

Figure 1:
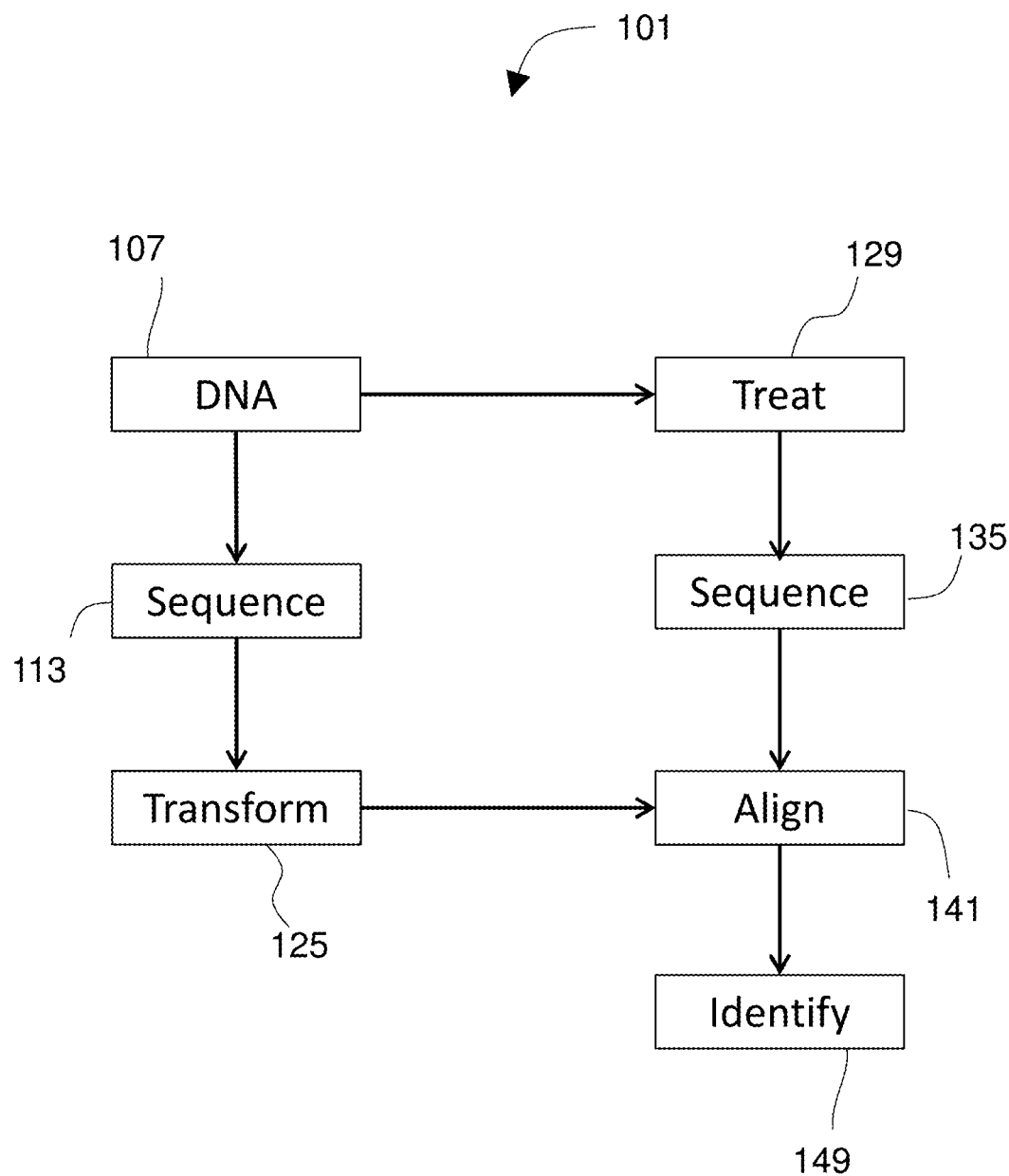
FIG. 1 diagrams a method for profiling epigenetic modifications in a genome.

FIG. 1 diagrams a method 101 for determining a pattern of epigenetic modifications in a genome. The method 101 includes obtaining a sequence 113 of nucleotide bases from nucleic acid 107 from a subject and transforming 125 the sequence into a graph. The graph is composed of vertices connected by edges and includes at least one path that splits into a first branch and a second branch, wherein the first branch represents a base observed in a position of the sequence and the second branch represents an alternative base not observed in the position. The first branch and the second branch may subsequently rejoin, e.g., just 3' to the position. A second sequence 135 is obtained from bisulfite-treated nucleic acid 129 from the subject and the method further includes determining an optimal alignment 141 between the second sequence and the graph and observing 149—in a position in the second sequence that aligns to the position in the sequence—a corresponding base that matches the base observed in the position. A report is provided that identifies a modified base at the position within the genome of the subject.

Figure 2:
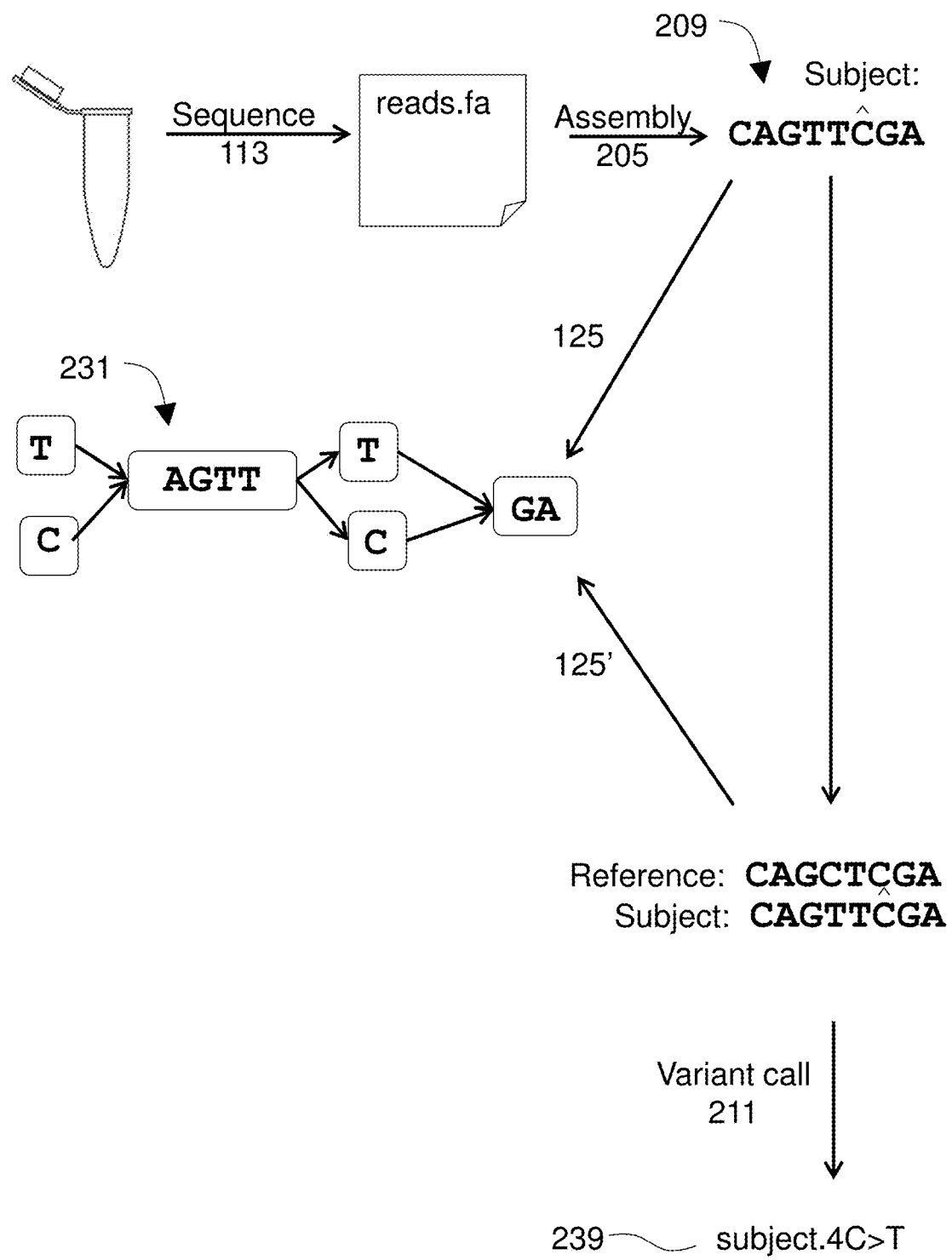
FIG. 2 illustrates transforming a sequence from a genome into a graph.

FIG. 2 illustrates obtaining 113 a sequence 209 from a genome of a subject and transforming 125 the sequence into a graph. FIG. 2 also shows that the obtained sequence 113 can be used in a variant calling operation 211.

In certain embodiments, sequence reads are obtained by performing sequencing on a sample from a subject. Sequencing may be by any method known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety. 454 sequencing involves two steps. In the first step of those systems, DNA is sheared into blunt-end fragments attached to DNA capture beads and then amplified in droplets. In the second step, pyrosequencing is performed on each DNA fragment in parallel. Addition of one or more nucleotides generates a light signal that is recorded by a CCD camera in a sequencing instrument.

Another example of a DNA sequencing technique that can be used is SOLiD technology by Applied Biosystems from Life Technologies Corporation (Carlsbad, Calif.). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

As shown in FIG. 2, sequencing 113 generates a plurality of reads. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 105 in a format such as FASTA, FASTQ, or similar.

Obtaining the sequence 209 may include the assembly 205 of sequence reads. Sequence assembly 205 may include any suitable methods known in the art including de novo assembly, reference-guided assembly, others, or combinations thereof. In a preferred embodiment, sequence reads are assembled 205 using graph-based alignment methods. See, e.g., U.S. Pub. 2015/0057946 and U.S. Pub. 2015/0056613, both incorporated by reference. Embodiments of a graph and its use are discussed in greater detail below. The result of assembly 205 is a sequence 209 representing the corresponding portion of the subject's genome.

All individuals (except identical twins) are genetically unique. Accordingly, systems and methods of the invention may be used for variant calling 211 to produce genotype information 239 about un-modified bases in the subject's genome (i.e., those bases in the subject's genome which differ from a reference genome). Any suitable variant-calling operation can be performed and a variety of variant calling operations are known in the art. For example, where the organism is a person, variant calling can include aligning sequence reads to a reference such as a DAG or the human genome referred to as hg18 and reporting SNP alleles in a format such as a Sequence Alignment Map (SAM) or a Variant Call Format (VCF) file. In certain embodiments, reads are aligned to hg18 using Burrows-Wheeler Aligner version 0.5.7 for short alignments, and genotype calls are made using Genome Analysis Toolkit. See Li & Durbin, 2009, Fast and accurate short read alignment with Burrows- Wheeler Transform. Bioinformatics 25:1754-60 and McKenna et al., 2010, The Genome Analysis Toolkit: a MapReduce framework for analyzing next-generation DNA sequencing data, Genome Res 20(9):1297-1303, the contents of each of which are incorporated by reference. Alignment to hg18 and variant calling produces results ("variant calls") that may be stored as a sequence alignment map (SAM) or binary alignment map (BAM) file—comprising an alignment string (the SAM format is described, e.g., in Li, et al., The Sequence Alignment/Map format and SAMtools, Bioinformatics, 2009, 25(16):2078-9). Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK). CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence. In a CIGAR string, each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). Additionally or alternatively, output from the variant calling may be provided in a variant call format (VCF) file. A typical VCF file 183 will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. Further discussion of methods for variant calling may be found in U.S. Pub. 2013/0073214; U.S. Pub. 2013/0345066; U.S. Pub. 2013/0311106; U.S. Pub. 2013/0059740; and U.S. Pub. 2012/0157322, the contents of each of which are incorporated by reference.

In a preferred embodiment, variant calling includes mapping the sequence to a reference graph, such as a directed acyclic graph (DAG) that represents known human genomic variation using methods and systems as described in U.S. Pub. 2015/0057946 and U.S. Pub. 2015/0056613, both incorporated by reference. Using alignment operations of the invention, reads can be rapidly mapped to a DAG despite their large numbers or short lengths. Numerous benefits obtain by using a DAG as a reference. For example, aligning against a DAG is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference DAG that may be used for variant calling is discussed in greater detail below. The optional variant calling 211 gives genotype information 239 about un-modified bases in the subject's genome.

For the epigenetic profiling, the sequence 209 is transformed 125 into a graph 231. As shown in FIG. 2, the graph 231 can be arrived at by transforming 125 the sequence 209 or by transforming 125' the sequence 209 after any alignment to a reference (be it a linear reference such as hg19 or a DAG as discussed above). For example, in certain embodiments, a subject's genotype information 239 (e.g., the set of variant bases in the subject's genome compared to the reference genome) may be incorporated into a graph. In these embodiments, new edges representing variation may be inserted into the graph (if not already present). In this way, the subject's genome is accounted for by the graph.

With continued reference to FIG. 2, it can be seen that a caret over a C is used within sequence 209 to represent what was a methylated cytosine within the original genome from the subject. At the stages of obtaining the sequence 209 and transforming the sequence 209 into the graph 231, it is not necessary to have any knowledge of the methylated cytosine and that mark is included in FIG. 2 to illustrate how systems and methods of the invention function.

In the depicted embodiment, the sequence 209 is transformed into the graph 231 (a "Methyl-Seq-ready graph") by creating nodes for sequence substrings and edges connecting the nodes. The graph may be created in the computer memory in that way or that relationship may be reversed with sequence stored in the edge objects. Creating the graph 231 further includes adding a single-nucleotide thymine branch as an alternative in place of every cytosine in sequence 209.

By allowing for the fact that cytosine may, post-bisulfite-treatment, be sequenced either as cytosine or thymine, using a graph here, pre-bisulfite treatment, is an excellent way to achieve unbiased and accurate alignment, and using a graph based on the subject's normal genome allows one to distinguish between C→T SNPs (which will show up as Ts in the alignment) from unmethylated cytosine nucleotides (which will only show up as Ts in the Methyl-Seq-based sequence). The latter point is important because in many cases the proportion of Cs methylated in a particular region will be the biologically-significant fact (e.g., will be the trigger for silencing a particular gene). As shown in FIG. 2, the variant calling 211 can provide genotype information 239 about un-modified bases in the subject's genome and thus, here, calls a genotype for the subject as g.4C>T (where the "4" would actually typically be distance from the beginning of the feature of interest (e.g., exon, gene, chromosome, etc). Regardless of the variant calling 211 operation, methods of the invention include transforming the sequence 209 into the graph 231 using a computer system with a memory subsystem storing the graph 231 in the memory subsystem.

Figure 3:
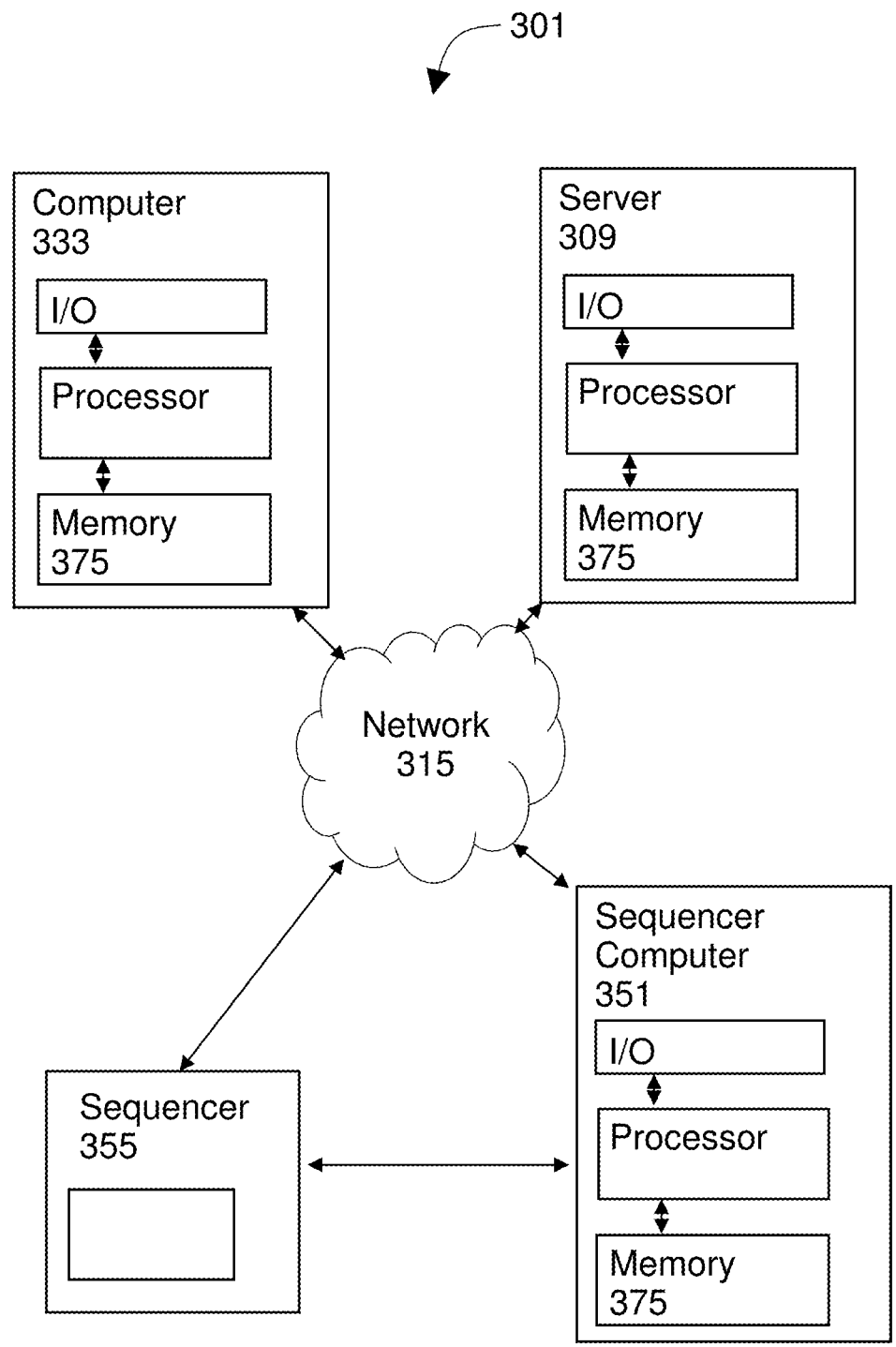
FIG. 3 illustrates a computer system for performing methods of the invention.

FIG. 3 illustrates a computer system 301 suitable for performing methods of the invention. The system 301 includes at least one computer 333. Optionally, the system 301 may further include one or more of a server computer 309 and a sequencer 355, which may be coupled to a sequencer computer 351. Each computer in the system 301 includes a processor coupled to a memory device and at least one input/output device. Thus the system 301 includes at least one processor coupled to a memory subsystem (e.g., a memory device or collection of memory devices 375). Using those mechanical components, the system 301 is operable to obtain a sequence generated by sequencing nucleic acid from a genome of a patient. The system uses the processor to transform the sequence 209 into the graph 231.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 375 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 301 is operable to produce a report (such as the report 801 of FIG. 8, described below) and provide the report 801 to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the graph 231 is stored in the memory subsystem using adjacency lists, which may include pointers to identify a physical location in the memory subsystem 375 where each vertex is stored. In a preferred embodiment, the graph 231 is stored in the memory subsystem 375 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

Figure 4:
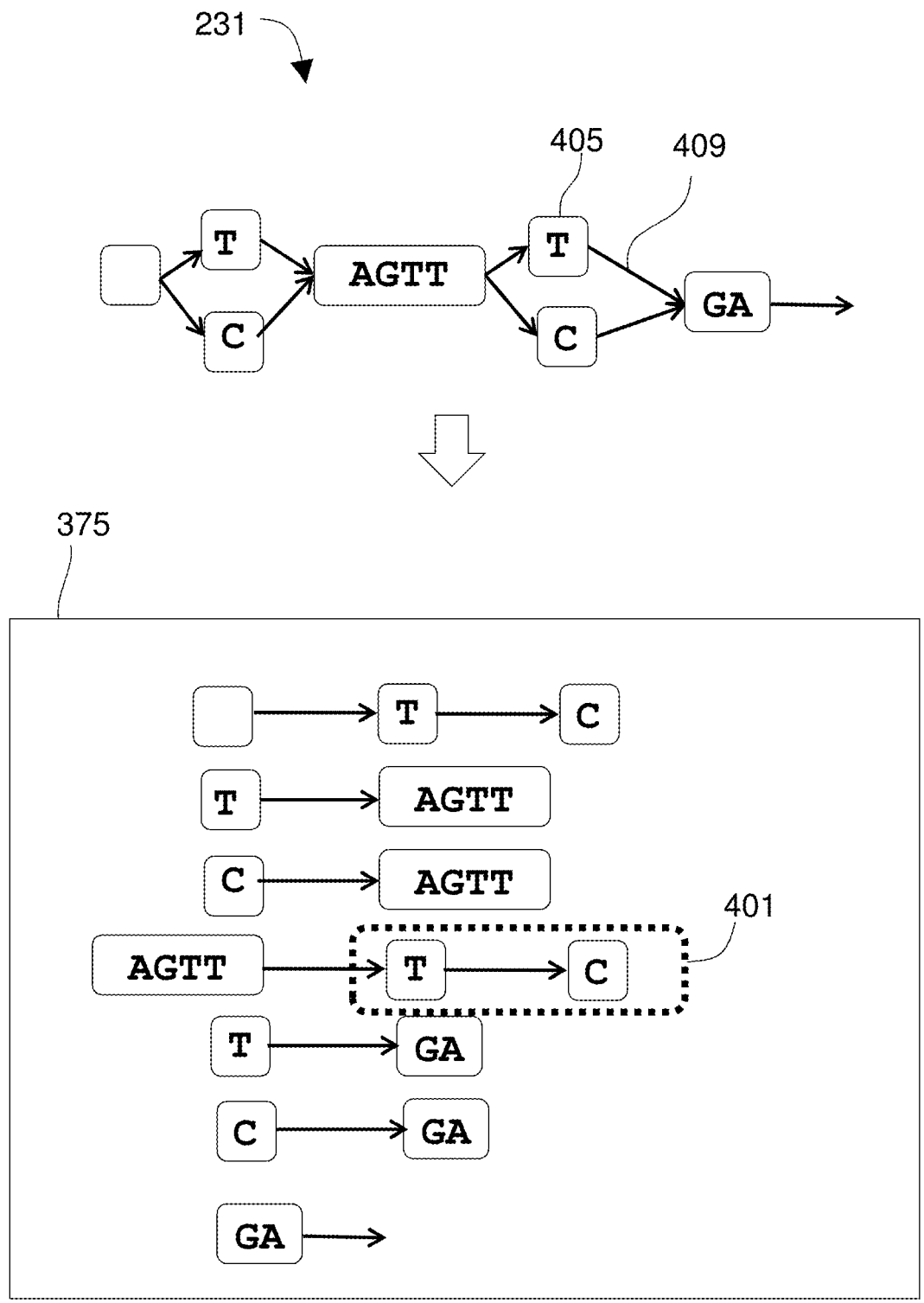
FIG. 4 shows the use of adjacency lists in an embodiment.

FIG. 4 shows the use of an adjacency list 401 for each vertex 405. The system uses the processor to create a graph that includes vertices and edges through the use of adjacency lists or index free adjacency. Thus, the processor may create the graph 231 using index-free adjacency wherein a vertex 405 includes a pointer to another vertex 405 to which it is connected and the pointer identifies a physical location in on a memory device where the connected vertex is stored. The graph 231 may be implemented using adjacency lists such that each vertex or edge stores a list of such objects that it is adjacent to. Each adjacency list comprises pointers to specific physical locations within a memory device for the adjacent objects.

In the top part of FIG. 4, the graph 231 is illustrated in a cartoon-like visual-friendly format. The graph 231 will typically be stored on a physical device of memory subsystem 375 in a fashion that provides for very rapid traversals. In that sense, the bottom portion of FIG. 4 is not cartoon-like and represents that objects are stored at specific physical locations on a tangible part of the memory subsystem 375.

Each node 405 is stored at a physical location, the location of which is in any adjacency list 401 that references that node. Each node 405 has an adjacency list 401 that includes every adjacent node in the graph 231. The entries in the list 401 are pointers to the adjacent nodes.

In certain embodiments, there is an adjacency list for each vertex and edge and the adjacency list for a vertex or edge lists the edges or vertices to which that vertex or edge is adjacent.

Figure 5:
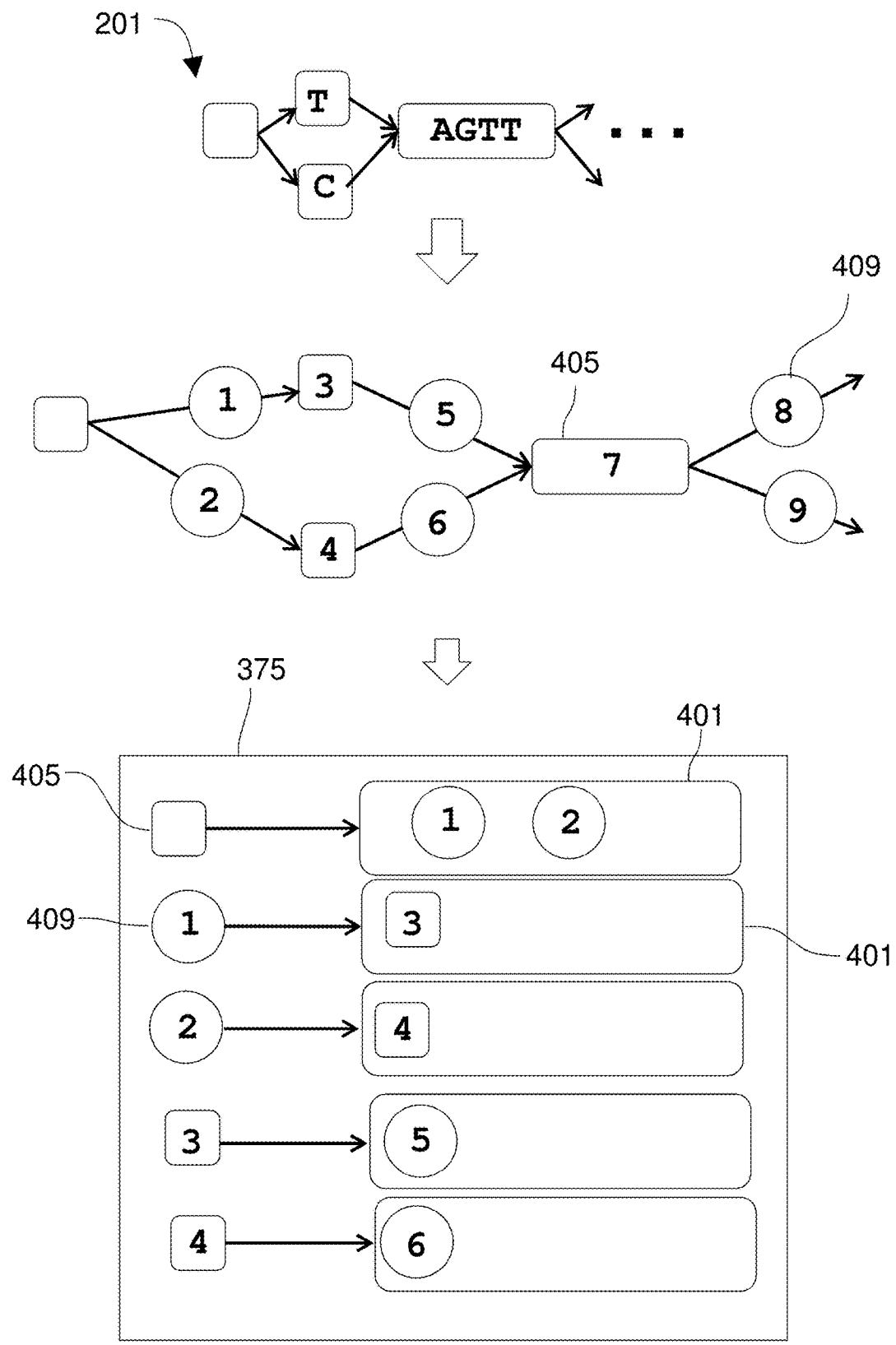
FIG. 5 shows the use of an adjacency list for each vertex and each edge of the graph.

FIG. 5 shows the use of an adjacency list 401 for each vertex 405 and edge 409. As shown in FIG. 5, system 301 creates the graph 231 using an adjacency list 401 for each vertex and edge, wherein the adjacency list 401 for a vertex 405 or edge 409 lists the edges or vertices to which that vertex or edge is adjacent. Each entry in adjacency list 401 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory but also dereferencing the pointer accesses intended data. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows sequence 209 to be queried against a genomic-scale genomic reference DAG (such as the DAG 231 of FIG. 2) containing millions of loci, using a computer system 301. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, incorporated by reference), which obviates the need for index look-ups, allowing traversals (e.g., as done in the modified SW alignment algorithm described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are in-fact references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale DAG (i.e., a graph 231 that represents all loci in a substantial portion of the subject's genome). Thus storing graph elements (e.g., nodes and edges) using a library of objects with native pointers or other implementation that provides index-free adjacency—i.e., embodiments in which data is retrieved by dereferencing a pointer to a physical location in memory—actually improves the ability of the technology to provide storage, retrieval, and alignment for genomic information since it uses the physical memory of a computer in a particular way.

While no specific format is required for storage of a DAG, FIGS. 4 and 5 are presented to illustrate useful formats. In illustrations below, exemplary DAGs are presented and discussed as graphs, but it will be appreciated that a DAG qua graph can be translated directly to a data structure in computer memory or a text document and back.

With reference back to FIG. 1, methods include transforming 125 the sequence into a graph 231 and also obtaining 135 a second sequence from bisulfite-treated nucleic acid 129 from the subject aligning 141 the second sequence to the graph 231. In some embodiments, nucleic acid from the subject is treated 129 and sequenced 135 to obtain the second sequence.

Figure 6:
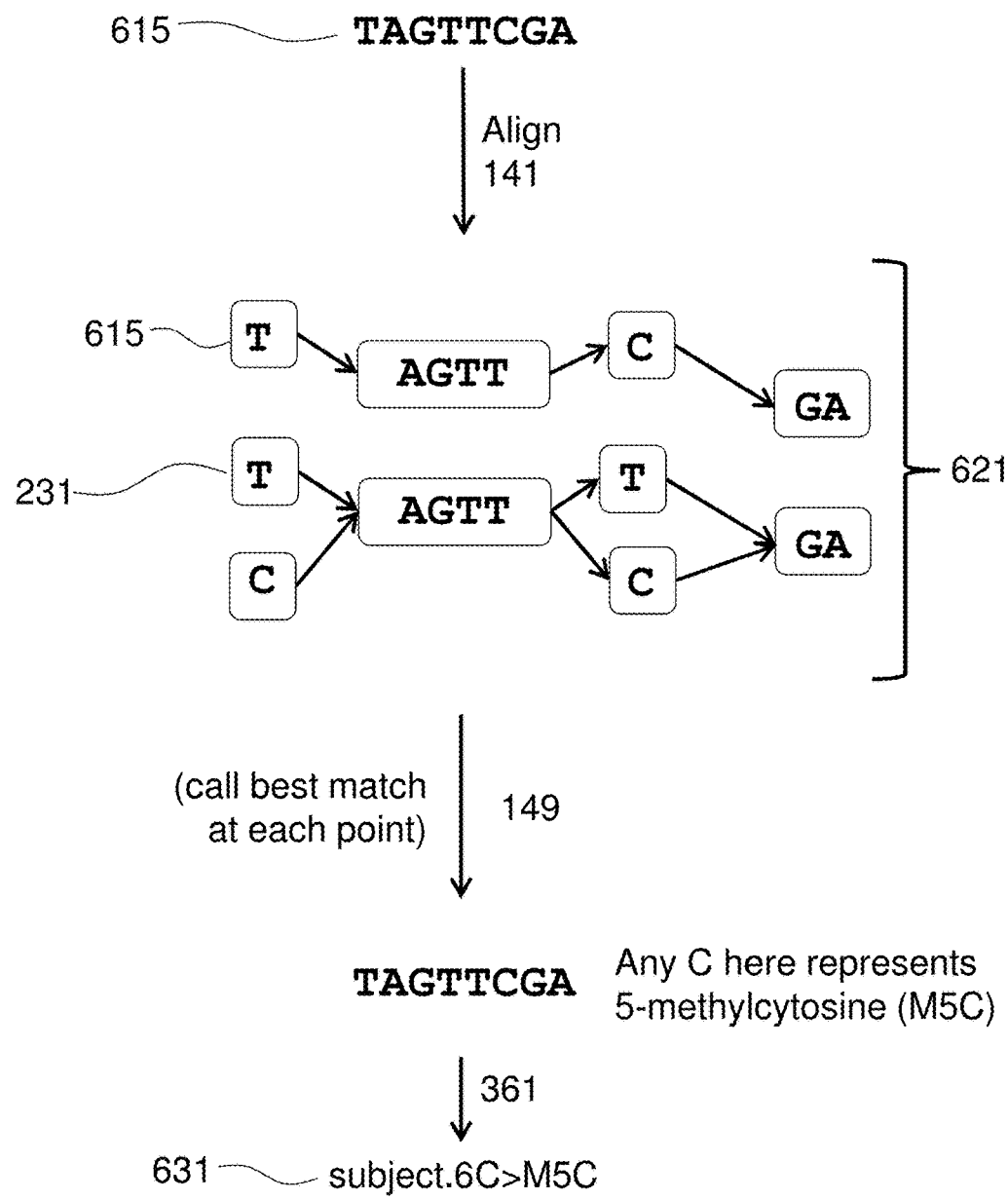
FIG. 6 diagrams obtaining the second sequence according to some embodiments.

FIG. 6 diagrams obtaining the second sequence according to some embodiments. FIG. 6 shows obtaining genomic DNA from a subject (e.g., blood sample, cultured cells, cultured bacteria, animal tissues etc.). The DNA may be isolated by using a commercially-available DNA extraction kit following the corresponding manufacturer's protocols.

In one embodiment, genomic DNA (1-10 μg) is dissolved in deionized water with 18 μl final volume. The DNA is denatured by boiling in a water bath for 20 min and adding 2 μl of 3 M NaOH and 380 μl 5 M sodium bisulfite solution. Mix, cover with mineral oil, incubate in dark at 50° C. for 12-16 h. Bisulfite treated DNA may purified using a Wizard DNA clean-up kit from Promega according to the manufacturer's protocol. The bisulfite-modified DNA is eluted in 50 μl deionized water and 11 μl 3 M NaOH is added. Incubate at 37° C. for 15 min to desulfonate the DNA. Add 166 μl 5 M ammonium acetate, 750 μl of absolute ethanol and 200 μl isopropanol to precipitate the DNA at −20° C. for 2-4 h. Centrifuge, wash with EtOH, and dry the DNA pellet. Re-suspend in TE or de-ionized water. Bisulfite PCR amplification can be performed as a regular PCR reaction. Prior to sequencing, purification of PCR products removes the residue of the PCR reaction that might interfere with the outcome of sequencing results. Commercially-available kits such as QIAquick PCR Purification Kit (Qiagen) can be used and the purified PCR products can be directly sequenced. If starting with single-molecules, it may be preferable to clone, e.g., using pGEM-T Easy vector system II (Promega), which provides a T4 DNA ligase system, a pGEM-T Easy vector and competent JM109 cells. Purified PCR products are ligated to the pGEM-T Easy vector and transformed into competent JM109 cells. The JM109 cells that carry the ligated vectors are selected on agar plates containing ampicillin/X-gal/IPTG by color and grown in LB medium. Plasmids containing the target DNA are extracted by using the QIAprep Spin Miniprep Kit (Qiagen) and subjected to standard sequencing analysis. All the procedures follow the manufacturer's protocol. For discussion see Li and Tollefsbol, 2011, DNA methylation detection: bisulfite genomic sequencing analysis, Methods Mol Biol 791:11-21; Li, 2007, Designing PCR primer for DNA methylation mapping, Methods Mol Biol 402:371-384; Li & Dahiya, 2002, MethPrimer: designing primers for methylation PCRs, Bioinformatics 18:1427-1431, the contents of each of which are incorporated by reference for all purposes. As shown in FIG. 6, methods of the invention may include sequencing 135 the bisulfite-treated DNA to produce the second sequence 615.

The second sequence 615 is aligned to the graph 231. This can include aligning the sequence reads produced by the sequencing 135 against the Methyl-Seq-ready graph 231 using, for example, a modified Smith-Waterman operation.

Performing the alignment 141 provides an optimal-scoring alignment 621. FIG. 6 shows a cartoon version of the second sequence 615 aligned to the graph 201. Making reference to the optimal scoring alignment 621, systems and methods of the invention may be used to observing 149—in a position in the second sequence 615 that aligns to the position in the sequence—a corresponding base that matches the base observed in the position. With continued reference to the alignment 621 illustrated in FIG. 6, it can be seen that the graph 231 includes two positions at which it splits into a first branch and a second branch, in which the first branch represents a base observed in a position of the sequence and the second branch represents an alternative base not observed in the position.

Using alignment 621 for example, systems and methods of the invention can be used to call 149 a methylated cytosine at any location in which C persists in the aligned sequence. To determine the optimal alignment 621, the sequence 615 may be aligned to the graph 621 using a modified Smith-Waterman operation that expands on the concept of a pairwise alignment.

Pairwise alignment generally involves placing one sequence along part of target, introducing gaps according to an algorithm, scoring how well the two sequences match, and preferably repeating for various position along the reference. The best-scoring match is deemed to be the alignment and represents an inference about what the sequence data represents. In some embodiments, scoring an alignment of a pair of nucleic acid sequences involves setting values for the probabilities of substitutions and indels. When individual bases are aligned, a match or mismatch contributes to the alignment score by a substitution probability, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i) |x'|=|y'|; (ii) removing spaces from x' and y' should get back x and y, respectively; and (iii) for any i, x'[i] and y'[i] cannot be both spaces.

A gap is a maximal substring of contiguous spaces in either x' or y'. An alignment A can include the following three kinds of regions: (i) matched pair (e.g., x'[i]=y'[i]; (ii) mismatched pair, (e.g., x'[i]≠y'[i] and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, $B(i,i)=1$ and $0<B(i,j)<1$ [for $i \neq j$] is one possible scoring system. For instance, where a transition is thought to be more biologically probable than a transversion, matrix B could include $B(C,T)=0.7$ and $B(A,T)=0.3$, or any other set of values desired or determined by methods known in the art.

Alignment according to some embodiments of the invention includes pairwise alignment. A pairwise alignment, generally, involves—for sequence Q (query) having m characters and a reference genome T (target) of n characters—finding and evaluating possible local alignments between Q and T. For any 1<i<n and 1<j<m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from O (m^2n) to O (mn) where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_0l = 0 \text{(for } 0 \le k \le n \text{ and } 0 \le l \le m) \quad (1)$$

$$H\_ij = \max\{H\_(i-1, j-1) + s(a\_i, b\_j), H\_(i-1, j) - W\_\text{in}, H\_(i, j-1) - W\_\text{del}, 0\}$$

(for 1≤i≤n and 1≤j≤m)

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{(for } 0 \le j \le m, \ 0 \le k \le n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$p[j, k] = \max(p[j-1, k-1], \quad (3)$$
$$i[j-1, k-1], d[j-1, k-1]) +$$
$$\text{MISMATCH\_PEN, if } S[j] \ne A[k]$$
$$\text{if } S[j] \ne A[k]$$
$$= \max(p[j-1, k-1], i[j-1, k-1], d[j-1, k-1]) +$$
$$\text{MATCH\_BONUS, if } S[j] = A[k]$$

the insertion argument i[j,k], is given by equation (4), below:

$$i[j,k] = \max(p[j-1,k] + \text{OPENING\_PEN}, i[j-1,k], d[j-1, k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:
MATCH_BONUS: 10
MISMATCH_PEN: −20
INSERTION_PEN: −40
OPENING_PEN: −10
DELETION_PEN: −5

The relationship between the gap penalties (INSERTION_PEN, OPENING_PEN) above help limit the number of gap openings, i.e., favor grouping gaps together, by setting the gap insertion penalty higher than the gap opening cost. Of course, alternative relationships between MISMATCH_PEN, MATCH_BONUS, INSERTION_PEN, OPENING_PEN and DELETION_PEN are possible.

In some embodiments, the methods and systems of the invention use a modified Smith-Waterman operation that involves a multi-dimensional look-back through the graph 231. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the DAG-type reference. That alignment algorithm identifies the maximum value for $C_{i,j}$ by identifying the maximum score with respect to each sequence contained at a position on the DAG (e.g., the reference sequence construct). In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic DAG system that employs physical memory addressing (e.g., through the use of native pointers or index free adjacency as discussed above). The combination of multi-dimensional alignment to a graph 231 with the use of spatial memory addresses (e.g., native pointers or index-free adjacency) improves what the computer system is capable of, facilitating whole genomic scale analysis and epigenetic profiling to be performed using the methods described herein.

The operation includes aligning a sequence, or string, to a DAG. For the purpose of defining the algorithm, let S be the string being aligned, and let D be the directed acyclic graph to which S is being aligned. The elements of the string, S, are bracketed with indices beginning at 1. Thus, if S is the string ATCGAA, S[1]=A, S[4]=G, etc.

In certain embodiments, for the DAG, each letter of the sequence of a node will be represented as a separate element, d. A predecessor of d is defined as:

(i) If d is not the first letter of the sequence of its node, the letter preceding d in its node is its (only) predecessor;

(ii) If d is the first letter of the sequence of its node, the last letter of the sequence of any node (e.g., all exons upstream in the genome) that is a parent of d's node is a predecessor of d.

The set of all predecessors is, in turn, represented as P[d].

In order to find the "best" alignment, the algorithm seeks the value of M[j,d], the score of the optimal alignment of the first j elements of S with the portion of the DAG preceding (and including) d. This step is similar to finding $H_{i,j}$ in equation 1 above. Specifically, determining M[j,d] involves finding the maximum of a, i, e, and 0, as defined below:

$$M[j,d]=\max\{a,i,e,0\} \quad (6)$$

where
e=max{M[j, p*]+DELETE_PEN} for p* in P[d]
i=M[j−1, d]+INSERT_PEN
a=max{M[j−1, p*]+MATCH_SCORE} for p* in P[d], if S[j]=d;
max{M[j−1, p*]+MISMATCH_PEN} for p* in P[d], if S[j]M As described above, e is the highest of the alignments of the first j characters of S with the portions of the DAG up to, but not including, d, plus an additional DELETE_PEN. Accordingly, if d is not the first letter of the sequence of the node, then there is only one predecessor, p, and the alignment score of the first j characters of S with the DAG (up-to-and-including p) is equivalent to M[j,p]+DELETE_PEN. In the instance where d is the first letter of the sequence of its node, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the DAG up-to-and-including d, plus an INSERT_PEN, which is similar to the definition of the insertion argument in SW (see equation 1).

Additionally, a is the highest of the alignments of the first j characters of S with the portions of the DAG up to, but not including, d, plus either a MATCH_SCORE (if the jth character of S is the same as the character d) or a MISMATCH_PEN (if the jth character of S is not the same as the character d). As with e, this means that if d is not the first letter of the sequence of its node, then there is only one predecessor, i.e., p. That means a is the alignment score of the first j−1 characters of S with the DAG (up-to-and-including p), i.e., M[j−1,p], with either a MISMATCH_PEN or MATCH_SCORE added, depending upon whether d and the jth character of S match. In the instance where d is the first letter of the sequence of its node, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for the sequence 209 by calculating not only the insertion, deletion, and match scores for that element, but looking backward (against the direction of the DAG) to any prior nodes on the DAG to find a maximum score.

As shown in the lower portion of FIG. 6, any C appearing in the second sequence 615 can be taken to represent a methylated cytosine in the genome of the subject. Since the graph 231 may be gene- or genome-scale (e.g., millions of base-pairs long at its longest path), aligning the second sequence 615 to the graph 231 reveals where within the subject's genome the methylated cytosine lies. Thus, systems and methods of the invention may be used for calling 149 modified residues in the genome to produce epigenetic information 631 that identifies one or multiple modified bases and their locations within the genome of the subject.

Figure 7:
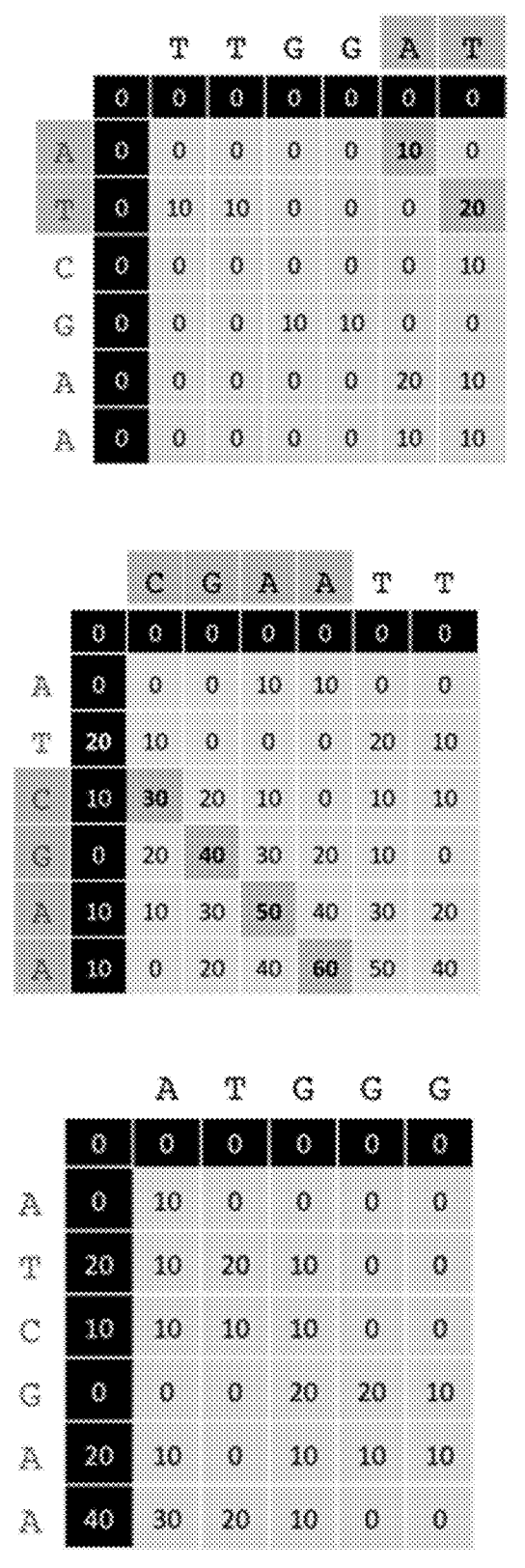

FIG. 7 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject.

Figure 8:
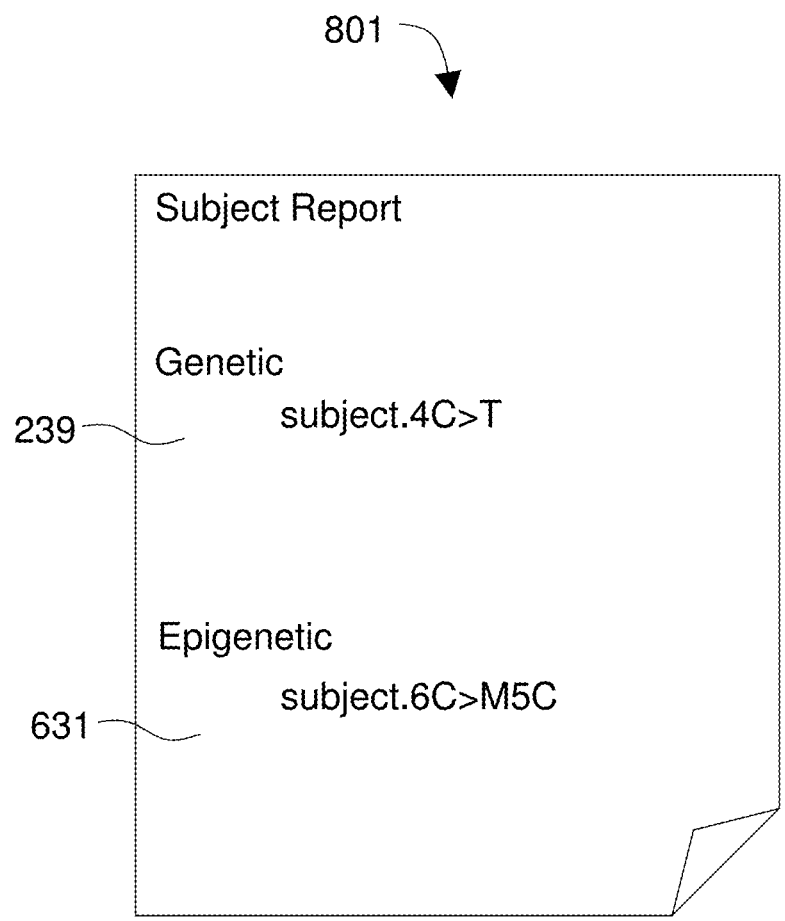
FIG. 8 illustrates a report profiling modified bases within the genome of the subject.

FIG. 8 illustrates a report 801 that identifies a modified base at the position within the genome of the subject. Report 801 includes epigenetic information 631 that identifies one or multiple modified bases and their locations within the genome of the subject. In certain embodiments, report 801 also includes genotype information 239 about un-modified bases in the subject's genome. Thus use of systems and methods of the invention provide a product that facilitates medical genetics and patient counseling. A physician may use a report 801 provided by the system to determine a medical course of action or counsel a patient on health and wellness issues.

Methods may be used to provide a report on phenomenon with clinical or developmental significance to a subject. For example, a report may identify a gene in the subject for which transcription has been regulated by the methylated cytosine at the position within the genome of the subject. In some embodiments, the report identifies a methylation status of a CpG island within the genome of the subject, for example, whether the CpG island is hyper- or hypo-methylated. Such a report may usefully determine whether CpG islands are hyper- or hypo-methylated, something that is often particularly biologically significant since CpG islands frequently occur in promoters of genes and hyper- or hypo-methylation of such sites can result in decreased or increased (respectively) expression of the associated genes.

It is understood that the addition of methyl groups to cytosine in certain CpG dinucleotides and patterns of methylated CpGs provide an epigenetic means for differential regulation of gene expression. It may be that CpG methylation regulates and stabilizes chromatin structure, influencing the ability of the transcription machinery to access regions of DNA. As a result, methylated CpGs may restrict transcription while unmethylated CpGs in the vicinity allow a gene to be expressed. Where a report 801 reveals a methylation status, such as a specific pattern, or hyper- or hypo-methylation, the report may provide insight into specific gene expression within a subject, and may be even be used to illustrate expression within specific tissue or cells. Discussion may be found in Saxonov et al., 2006, A genome-wide analysis of CpG dinucleotides in the human genome distinguishes two distinct classes of promoters, PNAS 103 (5):1412-1417, incorporated by reference.

It is noted that certain embodiments of systems and methods of the invention may be used for bisulfite conversion reaction that tend to be incomplete. In some treatments 129, incomplete bisulfite conversion may otherwise result in unmethylated Cs being called as methylated. Systems and methods of the invention may be used to address this problem by treating several different samples with bisulfite separately, and then sequencing and aligning as described above in connection with FIG. 6. Here, calling modified residues preferably includes calling a methylated cytosine at a position only when a C persists in each of the resulting aligned sequences. Additional discussion of methylation analysis may be found in Laird, 2010, Principles and challenges of genome-wide DNA methylation analysis, Nat Rev Genet 11:191-203; Zhang and Jeltsch, 2010, The application of next generation sequencing in DNA methylation analysis, Genes 1:85-101; and Lee et al., 2014, Improved reduced representation bisulfite sequencing for epigenomic profiling of clinical samples, Biological Procedures Online 16:1-9, the contents of each of which are incorporated by reference in their entirety for all purposes.

Figure 9:
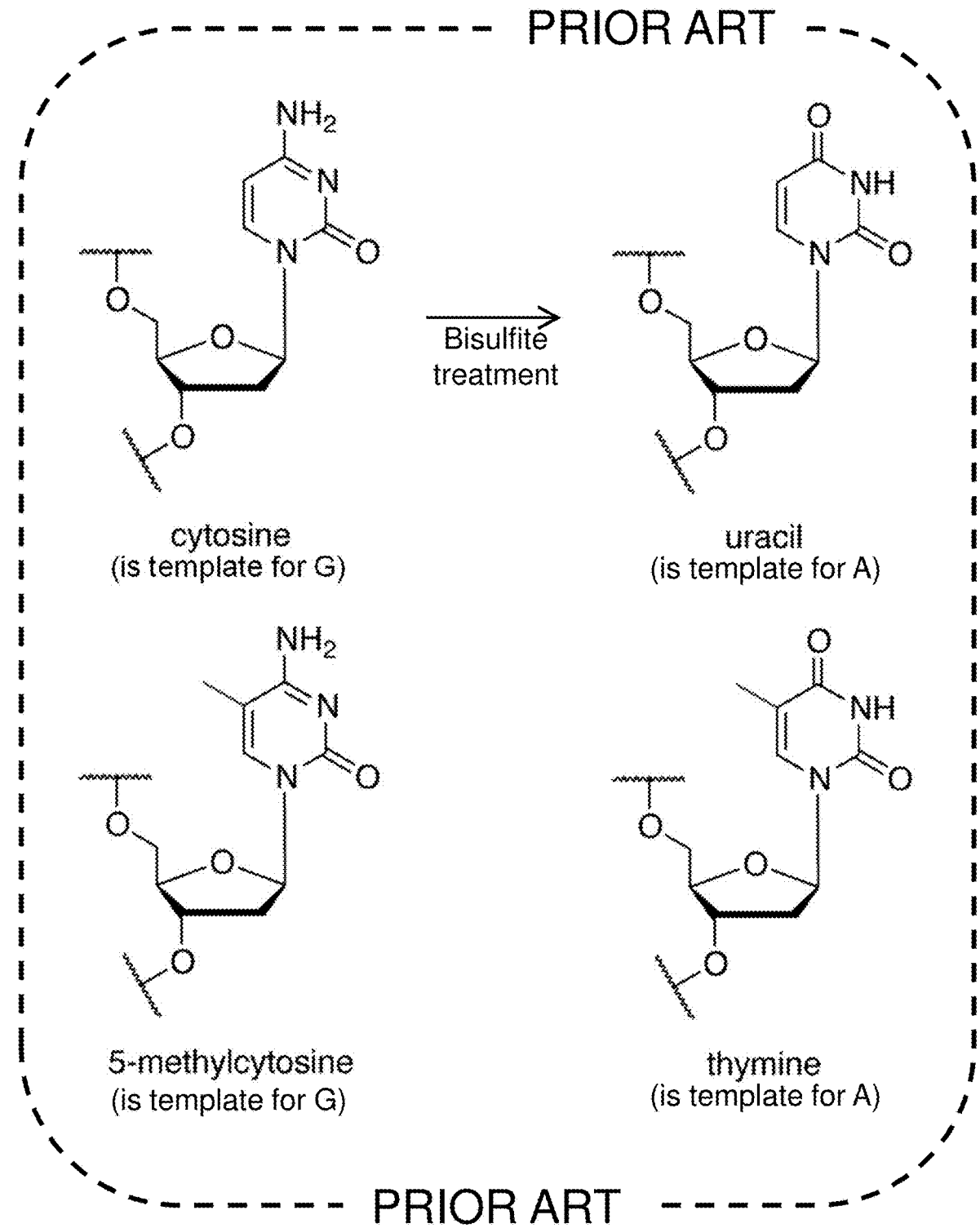
FIG. 9 gives a structure of certain pyrimidine nucleotides.

FIG. 9 gives a structure of common pyrimidine nucleotides that may be found in the subject genome to aid in visualizing the treatment and sequencing operations used in the invention. DNA methylation is a process by which a methyl group is added to a cytosine nucleotide. (Adenine nucleotides can also be methylated, but cytosine methylation is far more studied and better understood, so we will focus on cytosine methylation in this disclosure.) It typically occurs in CpG sites, i.e. when a C is followed in a genomic sequence by a G. Such groups are less prevalent than would be assumed given a random distribution of basepairs, something which may be attributed to the long-term effects of methylation. While deaminated cytosines are repaired, a methylated cytosine when deaminated is thymine, which is recognized as such during DNA replication. Thus after deamination, regions that had been methylated are not faithfully replicated and methylated CpGs in the germ line may be lost over time (Saxonov 2006). Methylation can affect the expression of a gene, typically repressing it, and is commonly implicated in cancer. In some contexts it may be heritable, and in this way it is also implicated in heritable diseases.

Methyl-Seq refers to the application of next-generation sequencing (NGS) methods to DNA that has been specially treated in order to make it possible to distinguish methylated from unmethylated cytosine. This involves treating the DNA with bisulfite, a process which converts unmethylated cytosine to uracil but leaves methylated cytosine unaffected. Remaining cytosine base-pairs can be assumed to be methylated. One complication is that the efficiency of the bisulfite conversion isn't absolute—some unmethylated cytosines will not be converted, and thus appear to be methylated.

Another complication that comes into play when using NGS methods is that PCR in the course of library preparation will turn the uracil nucleotides to thymine nucleotides, making it more difficult to recognize unmethylated cytosine and distinguish it from thymine (particularly thymine SNPs). (This happens because uracil binds with adenine in the first phase of PCR, and this adenine then bonds with thymine, which then bonds with adenine, etc.)

Additional material that may be useful in systems and methods of the invention may be found described in Lim et al., 2012, BatMeth: improved mapper for bisulfite sequencing reads on DNA methylation, Genome Biology 13:R82; Liu, 2012, Bis-SNP: Combined DNA methylation and SNP calling for bisulfite-seq data, Genome Biology 13:R61; Hoffman, 2005, Causes and consequences of DNA hypomethylation in human cancer, Biochem Cell Biol 83(3):296-321; and Zhang et al., 2011, Physical activity and global genomic DNA methylation in a cancer-free population, Epigenetics 6(3):293-299, the contents of each of which are incorporated by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for determining genomic modifications in a subject, the method comprising using at least one hardware processor connected to a tangible memory subsystem to perform:

obtaining a first sequence of nucleotide bases from nucleic acid from a subject, the nucleic acid representative of the genome of the subject;

creating, in the tangible memory subsystem, a directed acyclic graph (DAG), the DAG comprising a plurality of vertices stored as objects in the tangible memory subsystem, wherein each object comprises a sequence substring and a list of one or more pointers identifying a physical location in the tangible memory subsystem at which an adjacent object is stored, each sequence substring representing a nucleotide sequence, wherein at least one sequence substring comprises a plurality of symbols;

wherein creating the DAG further comprises creating at least one path that splits into a first branch and a second branch, which first branch and second branch subsequently rejoin, wherein the first branch comprises a first vertex representing a cytosine base observed in a position of the first sequence and the second branch comprises a second vertex representing a thymine base not observed in the position, the first vertex and second vertex each further comprising a pointer to a memory address containing a third vertex comprising a sequence substring from the subject's genome;

obtaining a second sequence from bisulfite-treated nucleic acid from the subject;

aligning the second sequence to paths through the DAG, wherein the aligning comprises calculating match scores between the second sequence and each of the sequence substrings associated with the first, second, and third vertices, and looking backward at each vertex against the direction of the DAG to any prior vertices if and only if a symbol comprises the first symbol of the string associated with its vertex to select a path with a maximum score;

identifying—in the alignment of the second sequence to the DAG—a corresponding cytosine base in the second sequence that matches the cytosine base observed in the position of the first sequence; and providing a report that identifies a methylated base at the position.

2. The method of claim 1, wherein the bisulfite-treated nucleic acid has received a bisulfite treatment that selectively converts unmethylated cytosine bases to thymine bases.

3. The method of claim 1, wherein the report further identifies an unmethylated version of the cytosine base at a different position in the genome of the subject.

4. The method of claim 1, wherein the DAG is created using an adjacency list for each vertex and edge, wherein the adjacency list for a vertex or edge lists the edges or vertices to which that vertex or edge is adjacent.

5. The method of claim 4, wherein each entry in the adjacency list is a pointer to the adjacent vertex or edge.

6. The method of claim 5, wherein each pointer identifies a physical location in the tangible memory subsystem at which the adjacent object is stored.

7. The method of claim 1, further comprising identifying methylated cytosines bases at a plurality of positions within the genome of the subject.

8. The method of claim 1, further comprising identifying other instances of methylated cytosine bases at positions within an entire gene of the subject.

9. The method of claim 1, further comprising:
performing a plurality of replicate bisulfate treating, sequencing, and alignment operations; and calling a methylated cytosine when a plurality of replicate sequences include a cytosine aligned to the position of the sequence.

10. The method of claim 1, wherein the report identifies a gene in the subject for which transcription has been regulated by the methylated cytosine at the position within the genome of the subject.

11. The method of claim 1, wherein the report identifies a methylation status of a CpG island within the genome of the subject.

12. The method of claim 1, further comprising identifying other instances of methylated cytosine bases occurring across at least 50% of a length of a chromosome of the genome of the subject.

13. The method of claim 1, wherein obtaining the second sequence comprises:
treating a portion of the nucleic acid from the subject with bisulfite; and
sequencing the bisulfite-treated nucleic acid from the subject.

14. The method of claim 1, wherein the sequence and the second sequence are derived from sequence reads generated by operating a nucleic acid sequencing instrument.

15. A method of identifying methylated cytosines bases in the genome of a subject, comprising using at least one hardware processor connected to a tangible memory subsystem to perform:

obtaining a plurality of sequence reads from bisulfite-treated nucleic acid from the subject;

determining an optimal alignment between each of the plurality of sequence reads and a genomic reference directed acyclic graph (DAG), the genomic reference DAG comprising a plurality of vertices stored as objects in the tangible memory subsystem, wherein each object comprises a sequence substring and a list of one or more pointers identifying a physical location in the tangible memory subsystem at which adjacent object is stored, each sequence substring representing a nucleotide sequence, wherein at least one sequence substring comprises a plurality of symbols;

wherein the reference DAG further comprises at least one path that splits into a first branch and a second branch, which first and second branch subsequently rejoin, wherein the first branch comprises a first vertex representing a cytosine base observed at a position of the genome of the subject, and the second branch represents a thymine base not observed at the position, the first vertex and the second vertex each further comprising a pointer to a memory address containing a third vertex comprising a sequence substring from the subject's genome;

wherein determining an optimal alignment comprises calculating match scores between the second sequence and each of the sequence substrings associated with the first, second, and third vertices, and looking backward against the direction of the DAG to any prior vertices if and only if a symbol comprises the first symbol of the sequence substring associated with its vertex to select a path with a maximum score;

identifying, in an optimal alignment between at least one sequence read and the reference DAG that aligns to the first vertex, a corresponding cytosine base that matches a cytosine base at the first branch; and providing a report that identifies a methylated cytosine at the position within the genome of the subject.

16. The method of claim 15, further comprising:
creating the genomic reference DAG by:
obtaining a plurality of sequence reads from nucleic acid from a subject;
determining, by a computer system comprising a processor, an optimal alignment between each of the plurality of sequence reads and the genomic reference DAG;
identifying, based on the alignment, positions in the subject's genome which have a base that differs from the genomic reference DAG; and
inserting a branch into the genomic reference DAG at the identified positions, in which the branch represents the base that differs from the genomic reference DAG.

17. The method of claim 15, further comprising:
identifying, in an optimal alignment between a second sequence read and the reference DAG, a corresponding thymine base that matches the thymine base at the second branch; and
providing a report that identifies an unmethylated cytosine at the position within the genome of the subject.

18. The method of claim 15, wherein the bisulfite-treated nucleic acid comprises a plurality of replicate bisulfite treating and sequencing operations; and further comprising calling a methylated cytosine when a plurality of replicate sequences include a cytosine aligned to the position of the sequence.

* * * * *

UNITED STATES PATENT AND TRADEMARK OFFICE
CERTIFICATE OF CORRECTION

PATENT NO. : 10,793,895 B2
APPLICATION NO. : 15/007874
DATED : October 6, 2020
INVENTOR(S) : Devin Locke et al.

Page 1 of 1

It is certified that error appears in the above-identified patent and that said Letters Patent is hereby corrected as shown below:

In the Claims

At Column 19, Claim 7, Line 60, please replace "cytosines" with --cytosine--.

At Column 19, Claim 9, Line 66, please replace "bisulfate" with --bisulfite--.

At Column 20, Claim 15, Line 25, please replace "cytosines" with --cytosine--.

Signed and Sealed this
Twenty-ninth Day of December, 2020

Andrei Iancu
*Director of the United States Patent and Trademark Office*